United States Patent [19]

Taylor et al.

[11] Patent Number: 4,725,963
[45] Date of Patent: Feb. 16, 1988

[54] METHOD AND APPARATUS FOR DIMENSIONAL ANALYSIS AND FLAW DETECTION OF CONTINUOUSLY PRODUCED TUBULAR OBJECTS

[75] Inventors: Morris Taylor; Ira Lon Morgan; Hunter D. Ellinger; Forrest F. Hopkins, all of Austin; Thomas Stephens, Leander, all of Tex.

[73] Assignee: Scientific Measurement Systems I, Ltd., Austin, Tex.

[21] Appl. No.: 732,301

[22] Filed: May 9, 1985

[51] Int. Cl.⁴ .................. G01N 23/02; G01B 15/06; G06F 15/46
[52] U.S. Cl. ......................... 364/507; 73/627; 378/20; 378/58
[58] Field of Search .................. 364/507, 414, 506; 378/15, 57, 58, 20, 901; 250/445 T, 360, 363 S, 361 R, 363 R, 369; 73/627, 628

[56] References Cited

U.S. PATENT DOCUMENTS

| | | | |
|---|---|---|---|
| 2,462,088 | 2/1949 | Friedman | 378/55 |
| 3,109,095 | 10/1963 | Van Horne | 378/54 |
| 4,187,425 | 2/1980 | Thompson | 378/59 |
| 4,284,895 | 8/1981 | Morgan et al. | 378/9 |
| 4,393,305 | 7/1983 | Shimizu et al. | 250/358.1 |
| 4,437,006 | 3/1984 | Morgan et al. | 250/363.5 |
| 4,600,998 | 7/1986 | Huet | 364/507 |

*Primary Examiner*—Felix D. Gruber
*Assistant Examiner*—H. R. Herndon
*Attorney, Agent, or Firm*—Jerry M. Keys

[57] ABSTRACT

An apparatus and method of non-contacting, non-destructive, on-line dimensional analysis and flaw detection of tubular products are disclosed. The apparatus includes penetrating radiation sources and detectors arranged about the product to be examined and a high-speed data processing system which employs novel computed tomography techniques to provide high precision dimensional estimates and flaw detection. The apparatus is capable of continuously determining the outside diameter, inside diameter, wall thickness, ovality, eccentricity, and weight-per-foot over a wide range of temperatures for essentially tubular products produced on a unit or continuous basis. The apparatus can also detect process-induced flaws in the products.

17 Claims, 12 Drawing Figures

THE SEVEN PARAMETERS NEEDED TO
DESCRIBE ECCENTRIC PIPE
X,Y- CENTER OF OUTSIDE CIRCLE
X',Y'- CENTER OF INSIDE CIRCLE
R - RADIUS OF OUTSIDE CIRCLE
R'- RADIUS OF INSIDE CIRCLE
$\rho$ - DENSITY OF METAL ILLUSTRATIONS OF RADIAL OPACITY
PROFILE EXPECTED FROM PERFECT PIPE
AND ECCENTRIC PIPE WITH FLAW.

⊗ Measurements used to compute outer $\theta_c$
☐ Measurements used to compute inner $\theta_c$
• Measurements not used

METHOD AND APPARATUS FOR DIMENSIONAL ANALYSIS AND FLAW DETECTION OF CONTINUOUSLY PRODUCED TUBULAR OBJECTS

BACKGROUND OF THE INVENTION

1. Field of the Invention

The present invention relates to a method of, and apparatus for, the continuous dimensional calculation and flaw analysis of manufactured tubular products in a non-contacting manner over a wide range of temperatures (0° F. to 3000° F.) by means of penetrating and computer-processed modeling algorithms.

2. Description of the Prior Art

In the manufacture of tubular products, such as seamless, extruded, stretched or welded pipe, it is important to measure the dimensions of the tube during its manufacture on a continuous basis at elevated temperatures to reject tube which fails to meet specifications and to provide information so that production errors can be promptly corrected to assure proper specifications of the final product. The more quickly the dimensional analysis can be made, the less tube produced will be out of specification, producing cost savings to the manufacturer. It is also desirable, when measuring the dimensions of the tube, that the measuring device be non-contacting with the tube, and that the measuring device be capable of producing continuous measurements, since the production of many tubular products is performed on a continuous basis.

In addition to dimensional analysis of manufactured tube, it is desirable to detect any flaws in the tubes that could lead to catastrophic failure once they are placed in use. Tubular products used in applications of high economic risk, such as power plants, aircraft, submarines, oil well casing and drill stems, require close scrutinization for flaws because failure of such products can result in costly losses of time, equipment, and possibly, personnel.

In the past, penetrating radiation systems have been used for non-contacting, non-destructive measurement of industrial products. In general, the radiation inspection techniques currently used involve the use of an x-ray or gamma ray source situated on one side of the tube to be inspected with a radiation detector located on the opposite side of the tube. The level of radiation intensity detected through the tube can be directly correlated to the average wall thickness of the tube. Such a system is illustrated in U.S. Pat. No. 2,462,088.

Various improvements have been made in the radioactivity inspection systems that produce more accurate and varied information regarding tube dimensions. By increasing the number of source-detector pairs, measurements of individual wall thickness and eccentricity can be obtained. Such systems are exemplified by U.S. Pat. Nos. 3,109,095 and 4,393,305. In U.S. Pat. No. 4,393,305 at least three source-detector pairs are arranged about the tube to be measured so that two of the radiation beams pass through each of three points to be measured on the tube. The measured values of radiation intensities detected can then be processed, using, for example, the method of least squares, as more specifically described in U.S. Pat. No. 4,393,305, to yield measurements of the inside diameter and the outside diameter (and, naturally, wall thickness) at the three points measured, as well as to indicate the eccentricity of the tube.

All of the radiation apparatus that have been previously developed to measure tube dimensions have the limitation of producing measurements at only a limited number of separate points about selected cross sections of the tube. The number of points that can be measured has been limited by the number of source-detector pairs that can be physically situated about the tube. Thus, previous tube examination systems have not provided measurement information for an entire cross section of tube. Further, the previous systems required that the tube be closely constrained to a particular position. Constraints added mechanical complexity, cost, and a significant source of measurement error. The constraining forces may also damage the product or slow the inspection process.

Previous tube examination apparatus can measure numerous points at a given cross section by rotating the source-detector pair relative to the tube and taking several sets of radiation intensity measurements. Such a system is exemplified in U.S. Pat. No. 4,187,425. However, the disclosed apparatus cannot provide complete cross sectional measurement information for a tube that is being continuously produced. Instead, such rotating systems produce measurements only along a helical path about the pipe when such systems are used in continuous production applications.

Recent developments have been made in the areas of Computed Tomography (CT), primarily in medical applications, that provide apparatus and methods for the examination of entire cross sections of objects. Theories used in this technology have application in the measurement and examination of industrial objects. Specific discussions of apparatus and methods for employing CT principles can be found in U.S. Pat. Nos. 4,284,895 and 4,437,006.

CT examination techniques provide advantages over previous pipe examination techniques in that they can be adapted to examine the complete cross section of the tube. Previous CT scanning apparatus such as those disclosed in U.S. Pat. Nos. 4,284,895 and 4,437,006, however, required that (1) the object to be examined be held stationary during the scans, and (2) in order to obtain accurate information regarding the cross section of the object, at least several hundred measurements needed to be taken by rotating the source-detector pair relative to the object.

Although the x-ray and gamma ray sources and detectors disclosed in these previous patents relating to CT scanning apparatus demonstrated the principles for rapid examination of cross sections of objects, such sources and detectors are not suitable for the rapid examination of cross sections of very opaque objects, such as many tubular products formed from steel. Changes in the sources in an effort to adapt such CT systems for denser objects may, in turn, render the previous detector systems unsuitable for such sources because improved pulse height discrimination is required, which necessitates an improvement in previous electronic discrimination techniques. Lastly, in order to rapidly obtain high precision dimensional measurements of roughly regular geometries without the necessity of several hundred sets of scans as is common in conventional tomographic reconstruction, a model had to be developed which could use data from fewer angle scans to generate the required high-precision dimensional measurements. In summary, the above-described limitations render previous CT examining apparatus less suitable for examining continuously produced objects such as seamless, extruded, stretched or welded tube for the purpose of making high-precision measurements of and detecting flaws in such tubular products.

SUMMARY OF THE INVENTION

The present invention provides a new and improved method of, and apparatus for, complete and continuous dimensional measurement and examination of continuously produced tubular, cylindrical or oval products, such as seamless or welded pipe, using penetrating radiation such as gamma rays and novel computer-assisted modeling techniques. The novel method for examination comprises transmitting a plurality of photons of penetrating radiation along a plurality of paths through the product to be examined, detecting the plurality of photons penetrating the product along each of the paths, generating signals representative of the number of photons detected along each path, and processing the signals generated by the detectors through use of a novel computer program which implements a novel modeling algorithm to obtain accurate values for the product's inside and outside diameters, ovality and eccentricity, as well as to detect flaws in the product, continuously as the product is produced.

The novel apparatus includes at least two penetrating radiation sources with known intensities disposed about the product to be measured for transmitting radiation along a plurality of paths through cross sections of the product, high-speed detector systems on the opposite side of the product from the sources for detecting the plurality of photons penetrating the product along each of the paths and generating signals representative of the number of photons detected, and a high-speed data processing system programmed to process the signals from the detector systems in accordance with a novel modeling algorithm which will obtain accurate values of the product's dimensions, as well as detect flaws, while the product is being continuously passed through the apparatus.

It is an object of this invention to provide a method of, and apparatus for, producing complete dimensional measurements of and detecting flaws in continuously produced objects, such as seamless or welded pipe.

Another object is to provide a method of, and an apparatus for, making such measurements and examination accurately without regard to pipe vibration or variations in temperature.

BRIEF DESCRIPTION OF THE DRAWINGS

FIG. 6b is an illustration of the radial density profiles expected from the perfect tube and eccentric tube of FIG. 6a;

DESCRIPTION OF THE PREFERRED EMBODIMENT

Figure 1:
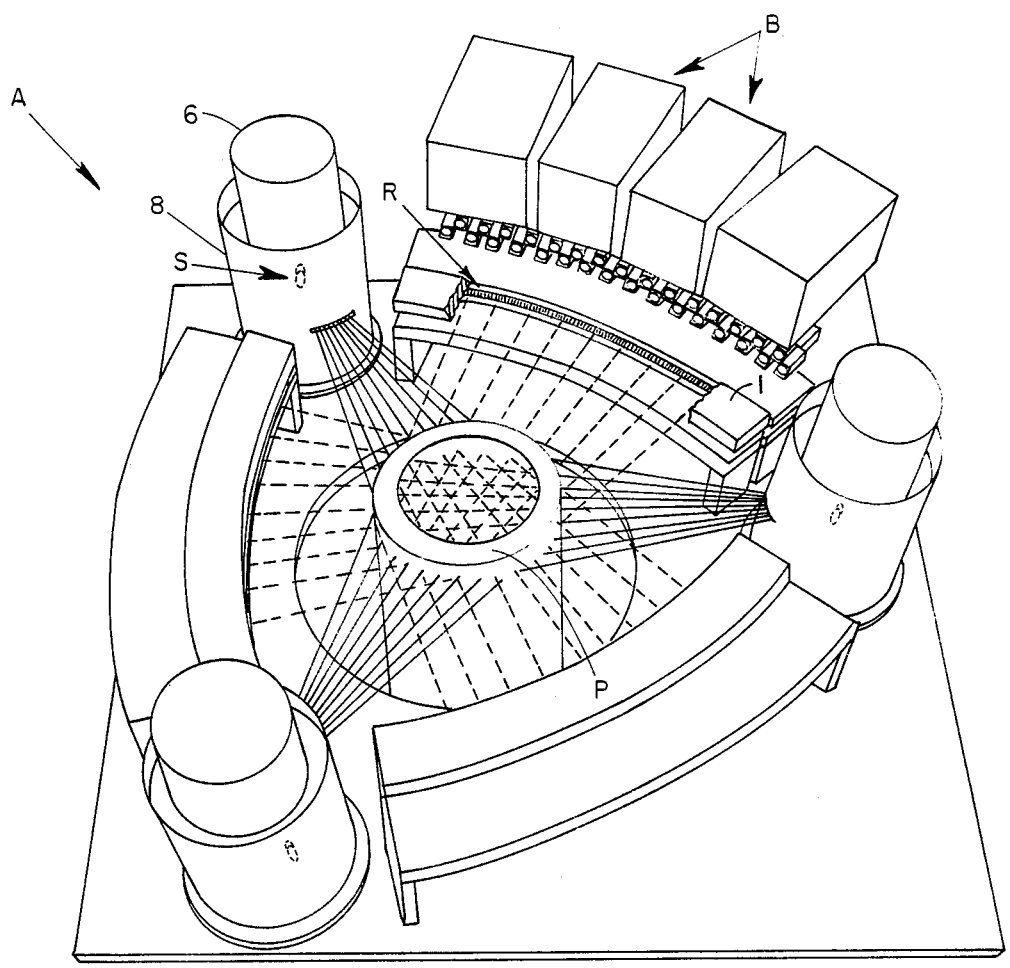
FIG. 1 is a simplified perspective representation of a suitable scanning apparatus for carrying out the present invention.
Figure 2:
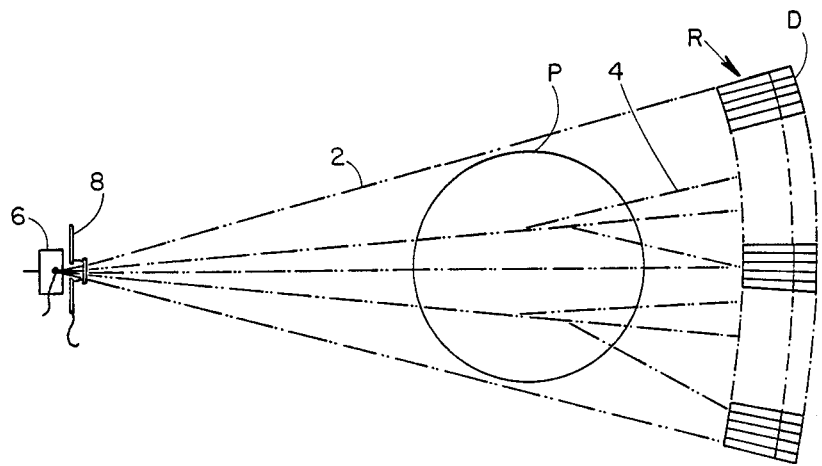
FIG. 2 is a simplified diagrammatic representation of a portion of the scanning apparatus of FIG. 1.

In the drawings (FIGS. 1 and 2), the apparatus A for the dimensional analysis of and flaw detection in tubular products P, such as seamless or welded pipe, has at least two, and preferably three, coplanar gamma ray sources S mounted at regular intervals on a baseplate B about an opening in its center through which the tubular product P can continuously travel. Each of the sources S transmits a fan beam through the product P to a detector array R of closely packed detectors D also mounted on the baseplate B directly opposite the source S. A parallel plate collimator 1 is placed in front of the detector array R to define the thickness of the fan beam. The detector arrays R are oriented relative to the sources to maximize the detection of the portion of the gamma ray photons which have passed through the product P without being absorbed, reemitted or scattered at angles greater than a few degrees as a result of collisions with the atoms of the material forming the product P. These photons will hereinafter be described as primary photons 2. The portion of the penetrating radiation either absorbed or deflected from the original paths to travel in any direction from the point of deflection along secondary paths are hereinafter described as secondary photons 4.

Reproducible beam optics for the apparatus A and provided by mounting the three sources S and their associated detector arrays R on a stiff support structure which can also function as a precision template for orienting the sources S and detector arrays R. A suitable support structure B is a 1.4-inch thick cast aluminum baseplate. The support structure B, in turn, may be mounted to an external structure, for example, by four 10-inch wide by 3-inch section aluminum channel beams (not shown). The locations of the sources S and detectors D thus can be controlled to an accuracy of ±0.001 inches at 25° C., which eliminates the need for mechanical position adjustment mechanisms. There are no dissimilar metals employed in the mechanical structure, so that although the actual dimensions may vary with temperature, the geometry of the beam optics are preserved.

The detectors D detect individual primary photons 2 which have passed through the product P from the source S along a plurality of paths which are substantially perpendicular to the surface of the detectors D directed at the source S. The detectors, however, may also detect unwanted secondary photons 4 which have been deflected from other paths. Although the detector array R and detectors D are designed to maximize the detection of primary radiation and minimize the detection of such secondary photons, these secondary photons may still have sufficiently high energies (although lower than the primary photon energies) to reduce the effectiveness of prior self-collimating detectors. This is primarily true when the dominant interaction process for generating secondary photons is Compton scattering rather than the photoelectric effect.

The detectors D transmit an analog signal representative of the individual photons (both primary and secondary) detected to a discriminator subassembly E (FIG. 3) which utilizes a novel discrimination technique to reject most of the remaining signals caused by detected secondary photons (i.e. all signals below a threshold level). The discriminator subassemblies E for the detectors D packed in a particular array R may be placed on suitable electronic boards or cards and slotted into suitable enclosures B. The threshold level setting for each individual discriminator is controlled by means of a threshold signal generated in a digital-to-analog converter 32 based on data received from the computer C. The computer C selects the threshold level signal for each individual discriminator subassembly E so that the actual count rate is a constant fraction of the count rate at which individual primary photons enter the detector. This adjustment is made when there is no product present between the sources S and detector arrays R.

The remaining primary photon signals from each discriminator subassembly E are counted and transmitted through a series of temporary storage buffers for temporary storage of the signals received from each of the detectors D during a predetermined sampling period, 10 milliseconds for example. After a very short time interval, 10 milliseconds for example, the signals are fed to the computer C for storage and processing. The computer C then processes the data from the detectors to determine the density of the product P along each of the various paths the photons traveled through the entire cross section of the product P. The computer C then utilizes a novel computer program which implements a novel modeling algorithm to generate high precision dimensional measurements of the product P with projections from only a few angles. In particular, the data is used to generate seven parameters, which parameters, in turn can be used to determine outside diameter, wall thickness, ovality, eccentricity and weight per unit length. The data then can be converted into various forms by conventional methods, such as numerical data, graphs or displays, for output on various types of output devices O.

I. SOURCE AND DETECTOR

The design parameters typically utilized in medical applications and in most industrial applications are limited to low density objects and are unsuitable for the successful application of computed tomography to the nondestructive evaluation of dense tubular products, such as seamless or welded pipe, during the production of such product on a continuous basis. The most significant difference in the scanning of dense inanimate objects is the necessity of using high energy photons, typically from a few hundred kiloelectron volts (Kev) to several million electron volts (Mev), in order to obtain sufficient penetration of the product P to yield a sufficiently high number of primary photon signals and thereby an adequate signal-to-noise ratio. The use of such high energy sources, in turn, cause beam hardening, when polychromatic sources such as X-ray tubes are employed, and the creation of numerous secondary photons 4 through Compton scattering, which may lead to unwanted detection of secondary photons 4 by the detectors D.

Methods currently used to reduce the amount of secondary photons 4 detected or to process detector signals to correct for the effects of such secondary radiation on the detectors, while satisfactory for low energy radiation, are inadequate for the examination of dense objects by high-energy radiation sources. Historically, mechanical collimators have been placed in front of detectors to limit the amount of secondary radiation detected. In addition, signals representative of secondary radiation can be measured using certain electronic calibration techniques and subtracted from the initial group of detector signals to achieve a high degree of scatter rejection, as exemplified by U.S. Pat. No. 3,937,965.

Other more recent methods and apparatus are disclosed in U.S. Pat. No. 4,284,895 wherein certain types of materials, such as scintillating plastic, can be configured into special geometric shapes and lined with relatively thin dense materials, such as lead foil, to shield the scintillators from secondary radiation such that the scintillators also act as collimators. While each of these methods is adequate in many cases, each has substantial drawbacks or inadequacies in the discrimination of secondary photons in the high energy range where Compton scattering is the dominant interaction process.

For example, the longer detector length required for efficient detection at these energies substantially increases the amount of scattered radiation potentially entering each detector. The larger amounts of shielding and/or collimation required to suppress scatter detection in this high energy range also substantially reduce the total active detection area that can be exposed to the source. This loss in the percentage of the detection area available for detecting photons is especially severe for smaller apertures, since the shielding width needed is constant. Further, the presence of collimators and shielding of greater width than the detection area of the detectors prevents detector configurations in which at least one detector in a closely-packed detector array in the plane receives primary photons from each portion of the cross section of the product under examination. Since such closely-packed detector configurations are required for complete (100%) inspection of an object for flaws in certain high-speed inspection tasks, this limitation is a severe one.

Correction of the detector signal by a value determined by calibration techniques also has substantial disadvantages in some cases. In addition to the extra processing time or circuitry involved, such correction always leaves a residue of extra noise even when the correct average value is subtracted. In cases (such as a thick flat edge) where the scattering from adjacent detectors into a detector produces a much larger signal than that resulting from direct transmission through the object, the residual noise can greatly diminish the accuracy with which the object's physical properties can be determined.

A more recent approach to scatter rejection is exemplified by the discrimination technique disclosed by U.S. Pat. No. 4,284,895. In that discrimination technique, a discriminator evaluates the signal generated and rejects signals below a certain threshold representative of secondary photons. A scaler following the discriminator counts those photons whose signal indicates that they came from primary photons.

This last approach also appears at first to be unpromising at the photon energy levels at which the creation of secondary photons is predominantly caused by Compton scattering rather than by the photoelectric effect due to the following:

(a) The practical rate at which individual photons can be counted is generally less than 100 megahertz, depending upon the detector material and electronics; this is much less than the photon rates available from many high enery photon sources.

(b) For high energy x-ray sources, which produce a continuous range of photon energies varying from the accelerating potential down to zero, it is difficult to distinguish whether a detected photon of average energy is a primary photon that was created with that energy or a higher energy photon which lost the difference in energy due to one or more Compton scattering interactions.

(c) For all the photons produced by typical x-ray tubes (and most of the photons produced by Ir-192, which is the most commonly-used isotopic source), the loss of energy in even wide-angle Compton scattering is so small that it gives very little basis for discrimination between primary and secondary photons caused by Compton scattering.

(d) Even if all high-energy photons had the same energy at the source, the fact that the interaction of the directly-transmitted or primary photons in the detector is itself a Compton scattering interaction (whose energy transmission to the detector depends on the random angle at which the photon is scattered) results in at least half of the directly-transmitted photons from many sources giving signals in a magnitude range that overlaps with the magnitude range of signals from photons that have undergone large-scale scattering before their interaction with the detector.

In summary, previous tomographic scanners are limited to the nondestructive evaluation of low density tubular products because (1) the sources previously used do not emit photons with sufficiently high energies to penetrate the dense materials from which many tubular products are made, and (2) previous detectors are less suitable for the detection of photons from typically used high energy radiation sources since Compton scattering is the dominant interaction process for the creation of unwanted secondary photons, and previous detection apparatus have difficulty discriminating between primary photons from such sources and secondary photons created through Compton scattering (in contrast to secondary photons created by the photoelectric interaction process).

Considering the present invention in more detail (FIGS. 1 and 2), the problems discussed above have been solved by selecting the source S to meet specific energy and spectral characteristics optimized for the density of the material being inspected and by using a modified version of the photon-counting, discrimination detector system disclosed in U.S. Pat. No. 4,437,006. More specifically, it has been found that in order for the photon counting detector system to fully discriminate against scattered photons, the sources used must emit a group of photons with energies of at least several hundred Kev which fall within an energy range that varies by no more than 15%, and is at least 50% more energetic than any other significant group of photons emitted at lower energies. Two gamma ray sources, Co-60 (50% at 1173 Kev, 50% at 1332 Kev) and Cs-137 (100% at 662 Kev), fit this description fully, whereas Ir-192, with three groups of photon energies emitted (67% at 310 Kev, 25% at 470 Kev and 8% at 605 Kev), does not. Thus sources S of Co-60 or Cs-137 are preferably used in sizes such that the required count rate of the detectors is no more than 10 megahertz (MHz). High energy photons from such sources S lose substantial energy when they scatter at angles of more than 45 degrees. For instance, the 1332 Kev photons from Co-60 lose 754 Kev in a 60 degree scattering. The *most* energy that such a scattered photon can transfer to the scintillators used with the sources S in a second scattering is 401 Kev. If the detector threshold is set to reject signals corresponding to this maximum energy, all scattering of more than 60 degrees will be rejected. Alternatively, the thresholds of these detectors can be reduced to simply reject unwanted electronic noise when a lower energy source is employed.

Preferably, the Source S is located in a source housing 6 having a suitable aperture through which the radiation is emitted. A fan collimator 8 of conventional design may be disposed about the source housing 6 to collimate the radiation to form a fan beam.

The detector array R of detectors D of the present invention may be constructed with substantially the same materials and in substantially the same way as those disclosed in U.S. Pat. No. 4,437,006, except as otherwise noted below.

The detectors D are preferably formed of blocks of scintillating plastic 10, such as NE 102 manufactured by Nuclear Enterprises. Each block or strip of scintillating plastic is also preferably 150 mm long and 4 mm wide. The lead absorption lining previously placed between the blocks of scintillating plastic 10 are no longer necessary in most applications of the apparatus of the present invention. The elimination of the lining also allows the scintillators to be packed more closely together, thereby allowing the receipt of more information about the product per projection. If a lining is used, a tungsten rather than a lead absorption lining is perferably disposed between the lateral surfaces of adjacent blocks of scintillating plastic due to the high energy photons being used. Thus, these scintillators may be made suitable for use over a broad band of source energies from a few Kev to several Mev.

Due to the rapid decay time of such fast scintillating plastic, the gamma ray photons detected by the scintillator will each generate a bundle of light photons. These bundles of light photons are then optically coupled to a photomultiplier 12 through a clear non-scintillating light pipe 14. The photomultiplier, in turn, generates an analog signal having an intensity proportional to the intensity of the light photons detected. Hence, the photomultiplier 12 generates a signal of varying magnitude which has peaks associated with the bundles of light photons.

II. DISCRIMINATOR SUBASSEMBLY

Figure 3:
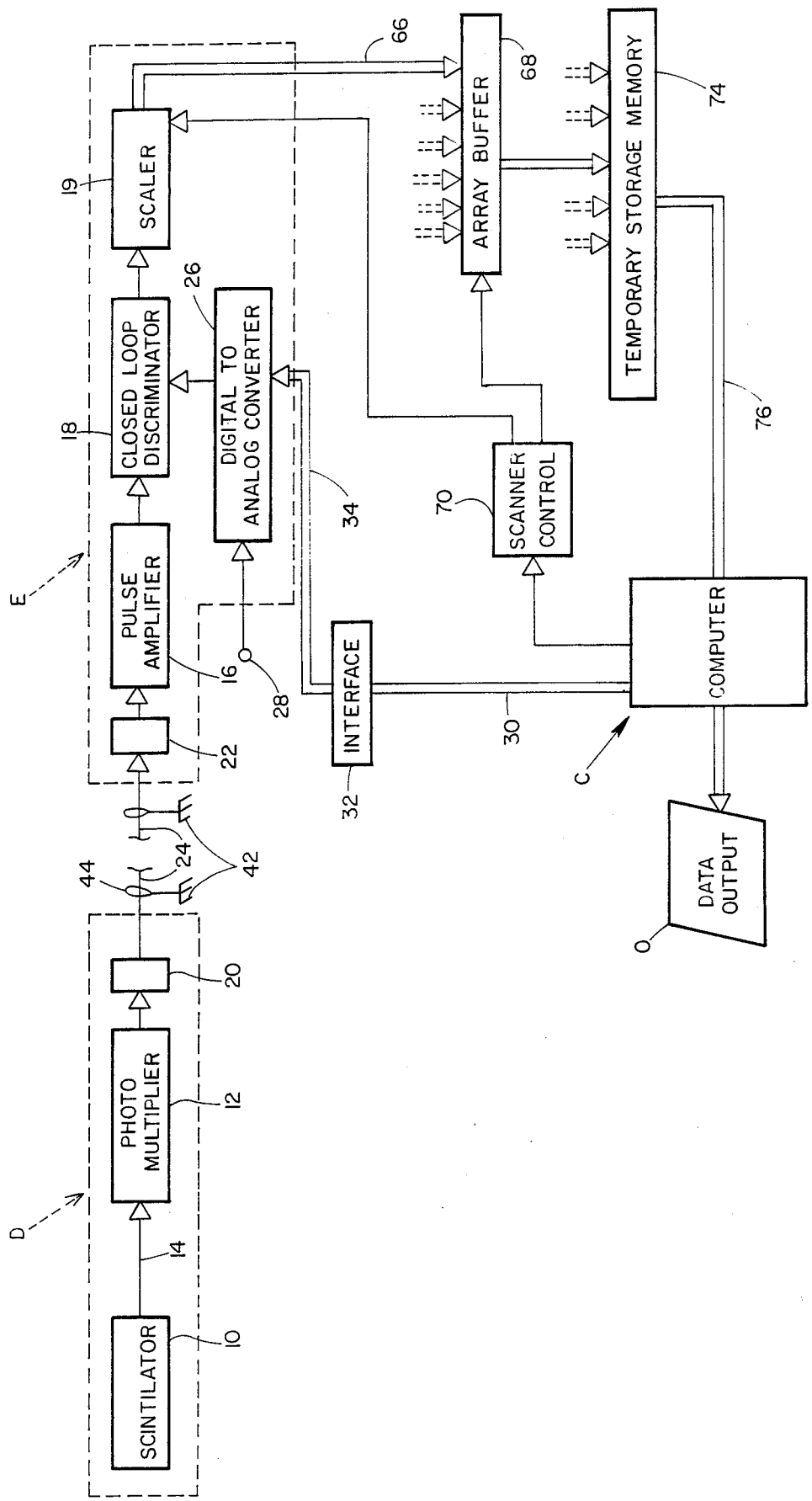
FIG. 3 is a schematic diagram of the part of the apparatus of the present invention for detecting penetrating radiation and generating the output signals representative of the radiation detected.

The signal from the photomultiplier 12 is electrically coupled to a novel discriminator subassembly E (FIG. 3). The discriminator subassembly electronically measures the magnitudes of the electrical impulses from the photomultiplier 12 and generates output pulses when the intensity of the input pulses are above a threshold level and then counts the output pulses above the threshold level to determine the number of primary photons which interacted with the scintillator 10 during a predetermined sampling period, e.g. 10 milliseconds.

The use of high energy sources needed for the scanning of dense tubular products presents several problems with existing discriminators. For example, scatter rejection comes at the expense of some efficiency loss because many primary photons will create signals from the photomultiplier smaller than the detection threshold of the discriminator. Thus, it may be desirable due to the limited number of projections obtained for a given product cross section to accept the detection of more scattered photons in order to detect a large percentage of the primary photons. Thus a variable discriminator level for each discriminator is desirable. Moreover, the variation in gain from detector to detector makes it necessary to have individually controlled threshold settings on the discriminators.

Due to these problems, the discriminator subassembly E is preferably constructed of a novel pulse amplifier 16, which also functions as a current-to-voltage converter, in order to generate well-formed pulses of the right magnitude within the fast response time required by a closed loop discriminator 18 for it to properly function without inducing oscillations in the discriminator 18 or amplifying noise in the input signal from the photomultiplier 12. The discriminator 18 generates digital signals in response to pulses from the pulse amplifier 16 that exceed an analog threshold level signal provided to the discriminator by a digital to analog converter ("DAC") 26. The digital output pulses from the discriminator 18 are coupled to a suitable conventional scaler 19. The scaler 19 counts the pulses received from the discriminator 18 and temporarily stores a digital signal representative of the total count within the sampling period in an output buffer internal to the scaler 19. This scaler signal represents the number of primary photons detected by the detector D in a given sampling period. A LSI 7061 integrated circuit manufactured by LSI Computer Systems, Inc., of Melville, N.Y., may be adapted for use as a suitable scaler 19.

The threshold signal is generated by the DAC, based upon a predetermined input reference voltage received at input 28 and an input value signal for the particular detector/discriminator channel provided by the Computer C. An AD7528JM integrated circuit manufactured by Analog Devices of Norwood, Mass., may be adapted for use as a suitable digital-to-analog convertor 26.

The computer transmits this input value signal through a serial data bus 30 to an interface 32 which then converts the serial data signal to a parallel data signal for transmission to the DAC over parallel data bus 34. The DAC needs this input value signal in order to generate the threshold signal for the discriminator 18. The computer selects the input value signal for each individual detector so that the actual count rate is a constant fraction of the count rate at which individual primary photons enter the detector. This adjustment is made when there is no product present between the source and detector.

Figure 4:
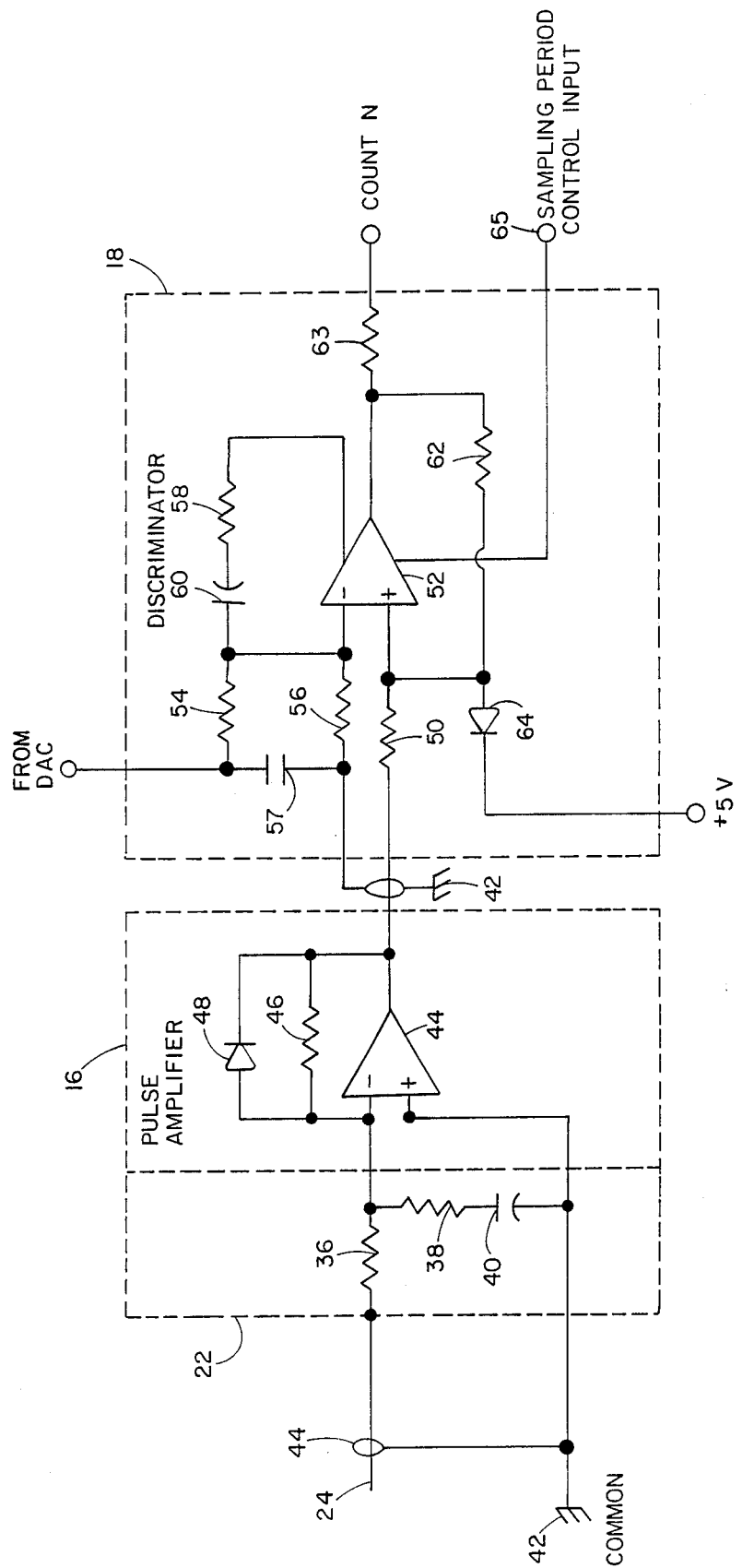
FIG. 4 is a circuit diagram of the pulse amplifier and closed loop discriminator used in the detector system of FIG. 3.

Considering the discriminator subassembly E in more detail (FIG. 4), the analog pulse signals from each photomultiplier 12 are coupled to the pulse amplifier 16 through a low impedance output matching network 20 of conventional design electrically connected to an input matching network 22 through a co-axial cable 24. To achieve the necessary response time, it is necessary to terminate the anode of the photomultiplier in a low resistance, typically 75 ohms. Accordingly, 75 ohms was selected as the impedance of the matching networks and the characteristic impedance of the coaxial cable. Since the pulse currents from the photomultiplier 12 are usually less than a milliampere, the voltage developed across the matching network 20 is usually less than 100 millivolts, with a significant proportion of the pulses being less than 10 millivolts.

The inner conductor of the coaxial cable 24 is electrically connected to resistor 36 of the matching network 22. The other end of resistor 36 is connected to the summing node of a differential operational amplifier 44, which node forms a virtual ground. A resister 38 and capacitor 40 are connected in series between the amplifier side of resistor 26 and a local reference voltage buffer common 42 which is the common ground for all discriminator subassembly channels on the same board or module. This common 42 is also connected to the outer conductor 44 of the cable 24 from the photomultiplier 12. The resistor 38 and capacitor 40 provide temporary charge storage during the initial response lag of the amplifier 16.

An HAI-2540-5 integrated circuit manufactured by The Analog Products Division of Harris Semiconducter located in Melbourne, Fla., may be adapted for use as a suitable differential amplifier 44. A resistor 46 and a diode 48 are connected in parallel between the summing node for the amplifier 44 and the amplifier output. Preferably the resistance of the resistor 46 is relatively large, 2K ohms for example. Initially a voltage builds up at the summing node until the amplifier 44 slews to a level at which an equal but opposite current flows through resistor 46 which exactly balances the input current through input resistor 36. For the duration of the remainder of the input current pulse, the summing node voltage is essentially zero.

As an equal but opposite current to the input flows through resistor 46, a voltage proportional to the current multiplied by the resistance of resistor 46 is generated by the amplifier at its output. Since resistor 46 is relatively large, a large magnitude voltage pulse appears at the output, greater than four volts, for example.

The diode 48 acts as a varactor, thereby providing rapid settling time to the baseline for the pulse tail. As the amplifier output rises at the pulse leading edge, the depletion region of the diode 48 increases, thereby reducing the capacitance and allowing the amplifier to slew faster. At the pulse tail of the signal, the original capacitance of the diode, 3 pF, for example, returns, thereby catching the slew rate and reducing undershoot.

In summary, the scintillator-generated signals from the photomultiplier 12 are transmitted as current signals to a pulse amplifier 16 with a low impedance input. The pulse amplifier then functions as a current-to-voltage converter by generating an output signal across a large resistance which is proportional to the current input. The actual output pulses from the amplifier 44, built within the design parameters disclosed herein, are approximately 4 volts with a half height width of 10 to $20 \times 10^{-9}$ seconds. It should be understood, however, that the preferred voltage output may vary depending upon the particular design of the discriminator 18 and scaler 19 and the count rate of the source S.

There are numerous advantages obtained from using pulse amplifier 16 rather than a conventional voltage amplifier to amplify and shape the pulses necessary for the proper functioning of the discriminator 18. For example, to perform threshold discrimination on the pulses from the photomultiplier, it is necessary to employ an extremely fast response voltage comparator in the discriminator 18. A common problem with such comparators is that some of the edge energy from the digital logic output from the discriminator becomes coupled back to the analog inputs of the discriminator, resulting in oscillations. The most common practice to suppress such instability is to incorporate a hysteresis in the circuit design to avoid the condition of having the analog inputs near their linear transform region.

To achieve a reasonable degree of system stability, the hysteresis loop magnitude at the discriminator 18 input must be above a minimum determined by the particular discriminator design, 10 millivolts for example. The voltage level from the photomultiplier falls below this minimum a significant portion of the time. Further, it is necessary to locate the discriminator very near the photomultiplier to avoid additional noise detection. This requires the discriminator to be located on the photomultiplier base assembly, an undesirable packaging situation. Additional noise associated difficulties arise in the incorporation of a variable threshold level discriminator design due to the low voltage levels which may occur at the comparator input.

One possible solution is to increase the signal level at the input of the discriminator an order of magnitude by either increasing the value of the photomultiplier anode terminator resistance or by amplifying the voltage developed across the terminator. Increasing the terminator resistance to a value sufficient to achieve a photomultiplier output level of at least one volt results in unacceptable pulse tailing. Alternatively, a voltage amplifier for the terminator voltage will work but presents its own set of problems. This amplifier, however, must still be located at the photomultiplier base to avoid cable loss and noise pick-up, and noise voltage will be amplified the same as signal voltage. Furthermore, any direct current (DC) instability in the amplifier output is amplified by the closed loop gain, presenting an offset voltage to the discriminator.

In summary, the pulse amplifier 16 provides several advantages over previous systems. First, the pulse amplifier 16 functions as an electrometer, i.e., a current-to-voltage converter. Induced noise signals tend to be "voltage" signals. The electrometer configuration results in a maximum voltage gain of unity. Voltage noise is thereby not amplified. Likewise, error due to amplifier input offset voltage is not amplified.

Secondarily, noise response is further reduced since noise pick-up on the co-axial transmission cable is received at the pulse amplifier as a common mode signal to the center conductor and the reference voltage common, which is to a large extent rejected by the differential amplifier 44. The remaining noise is not magnified due to the amplifier having a maximum voltage gain of unity. Finally, the amplifier functions as an active terminator to the transmission cable 24. Line termination characteristics are controllable by amplifier damping parameters. As the virtual ground from the summing node is propagated back to the anode of the photomultiplier, the amplifier 16 appears, to an extent, to be located near the photomultiplier anode.

Considering the discriminator 18 in more detail (FIG. 4), the output of the pulse amplifier 16 is coupled through a resistor 50 to the noninverting input of a voltage comparator 52. The threshold level signal from the digital-to-analog converter 26 is coupled through resistor 54 of a voltage divider formed by resistor 54 and resistor 56 to the inverting input of the voltage comparator 52. A suitable voltage comparator may be designed using an AM686HC integrated circuit manufactured by Advanced Micro Devices of Sunnyvale, Calif. which has the circuit equivalent of a Schottky-clamped NPN linear front-end and a Schottky TTL output stage.

If the input voltage level from the pulse amplifier 16 at the noninverting input of the comparator 52 exceeds the minimum threshold voltage signal at the inverting input, the comparator is turned on. A pulse is generated at the comparator "true" output after a short lag time, e.g. approximately $8-12 \times 10^{-9}$ seconds. A resistor 58 and capacitor 60 is coupled in series between the "not-true" output and the inverting input in order to provide a positive feedback signal to the inverting input. This feedback signal ensures that the output pulse has the minimum pulse width required by the scaler 19 to count the pulse, $20 \times 10^{-9}$ seconds. A suitable DC hysteresis, 4 millivolts, is provided through a voltage divider formed by input resistor 50 and resistor 62 connected between the noninverting comparator input and the "true" output. A diode 64 connected between the noninverting comparator input and a power source, 5 volts for example, prevents the output signal from the pulse amplifier 16, as seen at the input to the comparator 52, from exceeding the power source of the voltage comparator. An input voltage is provided to the voltage comparator at input terminal 65 to inhibit its operation during specified time periods, thereby controlling the sampling period.

The positive threshold level signal provided to the discriminator 18 from the DAC 26 has a magnitude determined in accordance with the following formula:

$$V = (-V_R \text{ at input 28}) \times \frac{\text{input value from computer}}{\text{full scale value set by the } DAC}$$

Thus, the computer C is capable of controlling each detector/discriminator channel threshold signal individually. The reference voltage $V_R-$ at input 28 is a hardware variable controlling all detector channels, thereby allowing simultaneous adjustment of the threshold range of all detector channels as the application may warrant.

The discriminator 18 provides for several advantages over prior discriminators. First, it provides closed loop control of the low-limit threshold signal. As a result, the discriminator 18 allows for on-line dynamic rejection of secondary photon signals, and for periodic automatic equalization of photomultiplier effective gain, without the necessity of varying any photomultiplier parameters, such as high voltage, dynode trim, etc. Another advantage of the discriminator 18 is that it eliminates any requirement for electronic alignment of discriminator threshold levels. This also means that maintenance of the apparatus is simplified since immediate interchange of plug-in modules may be done without recalibration.

In the preferred embodiment, the following resistors, capacitors and diodes may be used in the construction of the discriminator subassembly E:

resistor 36—75 ohms
resistor 38—75 ohms
capacitor 40—15 picofarad
resistor 46—2000 ohms
diode 48—IN4148
resistor 54—1000 ohms
capacitor 57—0.01 microfarad
resistor 58—470 ohms
capacitor 60—5 picofarad
resistor 62—10,000 ohms
diode 64—IN4148

III. PROCESSING

Conventional tomographic reconstruction images of cross sections of objects are normally based on data obtained from several hundred projections of the cross section under examination at numerous angles. While many of the details of conventional CT reconstruction methods are employed in the method of the present invention, other aspects of the methods must be modified in order to generate high-precision measurements of the dimensions and density of continuously produced tubular products due to the limited data that can be generated from a few projections of the product P from a limited number of angles as it passes through the scanning apparatus A.

Figure 6A:
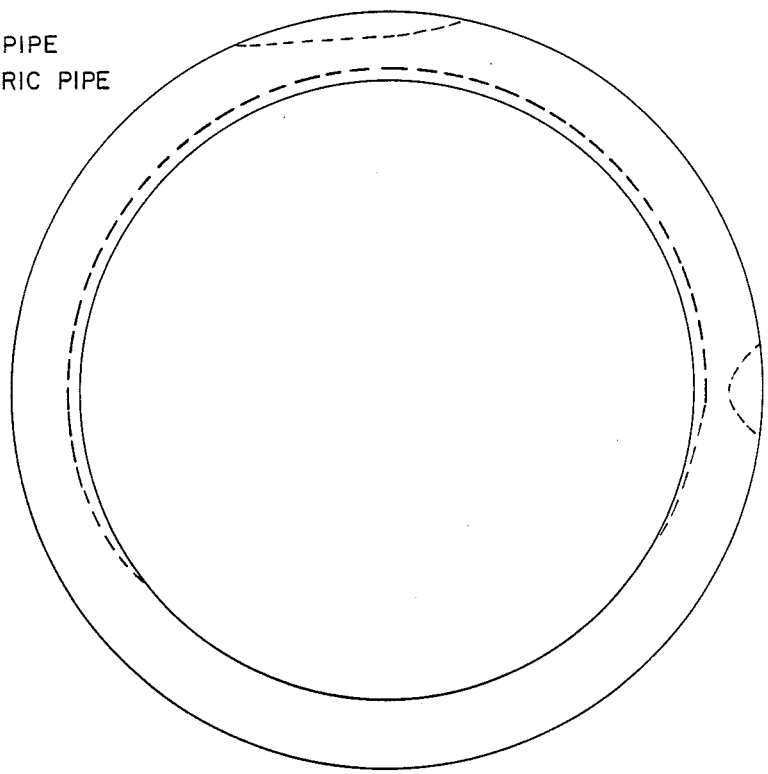
FIG. 6a is a cross section view of perfect and eccentric pipe.
Figure 6B:
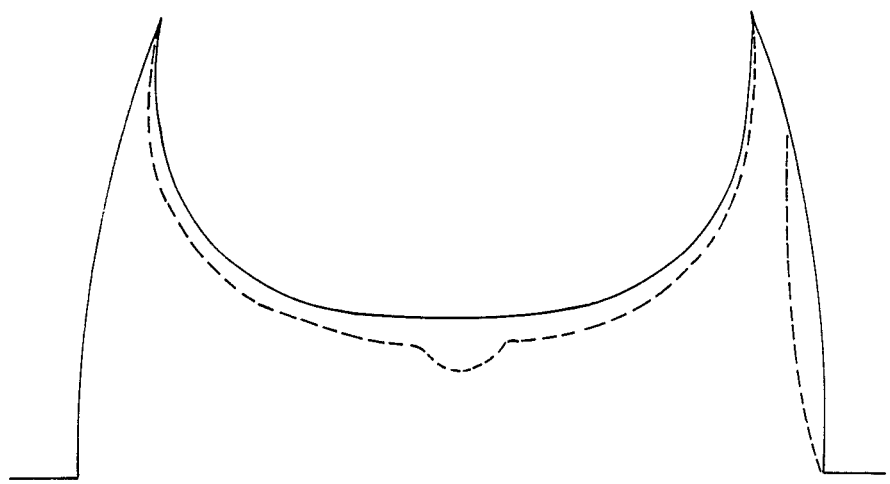

FIG. 6b illustrates the radial density profile of a cross section of a perfectly symmetrical tube shown in FIG. 6a, as observed from one angle. The profile will be identical for any other angular projection. For imperfect tube, some information about the imperfections will be contained in the profile at each projection with certain favored projections containing the most information. By choosing two or more regularly spaced projection angles, at least one profile will contain a highly visible anomaly due to the imperfection. For example, a projection profile made from eccentric tube is shown by the dotted line in FIG. 6b. The eccentricity of the tube is evidence from the variation of the peak width and peak height. A flaw in the eccentric tube is also clearly evident as a high frequency fluctuation in the central region of the density profile in FIG. 6b.

Density data generated from scans from two or three angles is not enough to calculate a full tomographic recontruction of high accuracy. In an object of uniform or known density and relatively simple geometry, such as a tubular product, the description of the object can be simplified so that the number of independent variables is reduced to fewer than the number of measurements. A simplified computer-implementable model offers the fastest and most accurate method of estimating dimensions from projection measurements.

Figure 7:
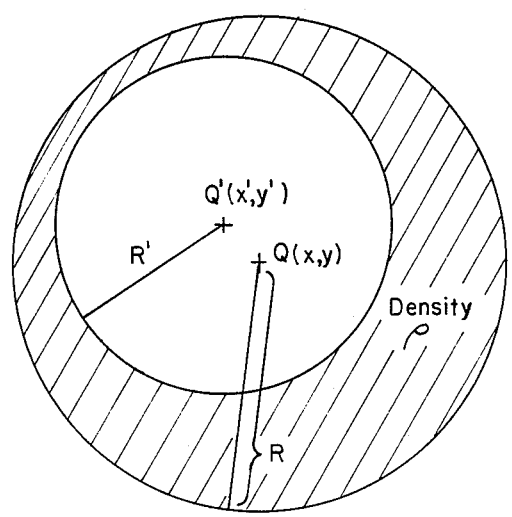
FIG. 7 is a diagrammatic representation of the seven parameters needed to describe eccentric tube.

The utility of the model depends on the extent to which the object to be examined can be described by a small number of parameters. A perfect tube could be described by five parameters: the two diameters, the density, and the coordinates of the centers of the inside and outside circles forming the tubular product. However, one may also model specific defects. Eccentricity measurements (the distance between the centers of the inside and outside circles) can be accommodated by two more parameters in the model for a total of seven parameters. The seven parameters needed to describe an eccentric pipe are shown in FIG. 7. The computer program employed in the first embodiment of this invention employs these seven parameters.

Figure 5:
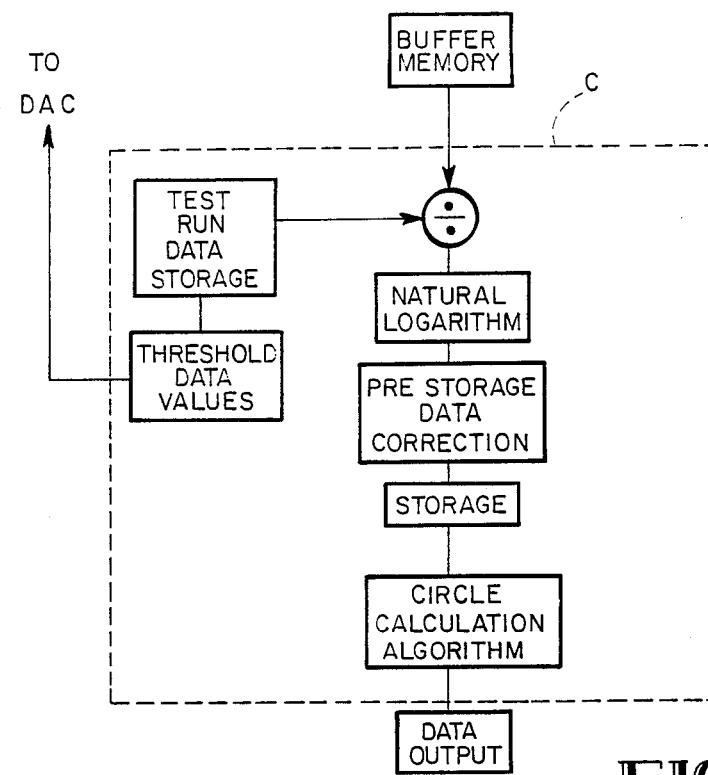
FIG. 5 is a schematic diagram of the computer-based processing steps for processing the output signals from the detector of FIG. 3.

Considering the computer-assisted process in more detail (FIGS. 3 and 5), the scaler 19 in each discriminator subassembly E in an array R transmits a digital signal representative of the number of primary photons detected during an exposure through a parallel data bus 66 to an array buffer 68 in response to a control signal from a scanner control circuit 70. After a preselected time to allow each scaler in each array to transmit its data to its array buffer, for example 10 milliseconds, and in response to another control signal from the scanner control 70, all three array buffers transmit all of their data over another parallel data bus 72 to a temporary storage memory 74 where it can be temporarily stored until the computer C can receive it over a CPU data bus 76. Preferably, such signals are transmitted in parallel over both busses to decrease transmission time.

Since the signals from each of the detectors D represent the intensity I of the primary radiation passing through a given cross section of the product P along a particular path, the average density or opacity of the product P along any particular path from the source S to a particular detector D in an array R may be represented in accordance with the following conventional formula:

$$I = I_0 e^{-\mu \rho p_i}$$

where
$I_o$ = the initial intensity signal generated by the same detector D during an initial test run without the product P being placed between the source S and detector D
$p_i$ = distance through the object along a given path in centimeters
$\mu$ = the mass absorption coefficient in cm$^2$/gram
$\rho$ = the density in grams per cubic centimeter.

Thus the computer can solve for the average density along a given path, in accordance with $$\mu \rho p_i = \ln I_0/I$$

Pre-storage correction of this signal is then accomplished using correction factors experimentally developed for the particular apparatus during test runs without product P in place. These corrections eliminate non-linearities in the signals and also eliminate errors resulting from minor misalignments of the sources S and detectors arrays R. Errors caused by the response function of the discriminator subassembly E can also be eliminated at this stage. The corrected signals are then placed into computer storage. If multiple projections are taken, the digital signals for each projection are stored until the end of the examination.

After all data from the scanning of a cross section of the product P is stored, the computer C determines the measurements for the particular cross section of the tube in accordance with the steps of a computer program which implements a novel circle calculation algorithm.

Figure 8A:
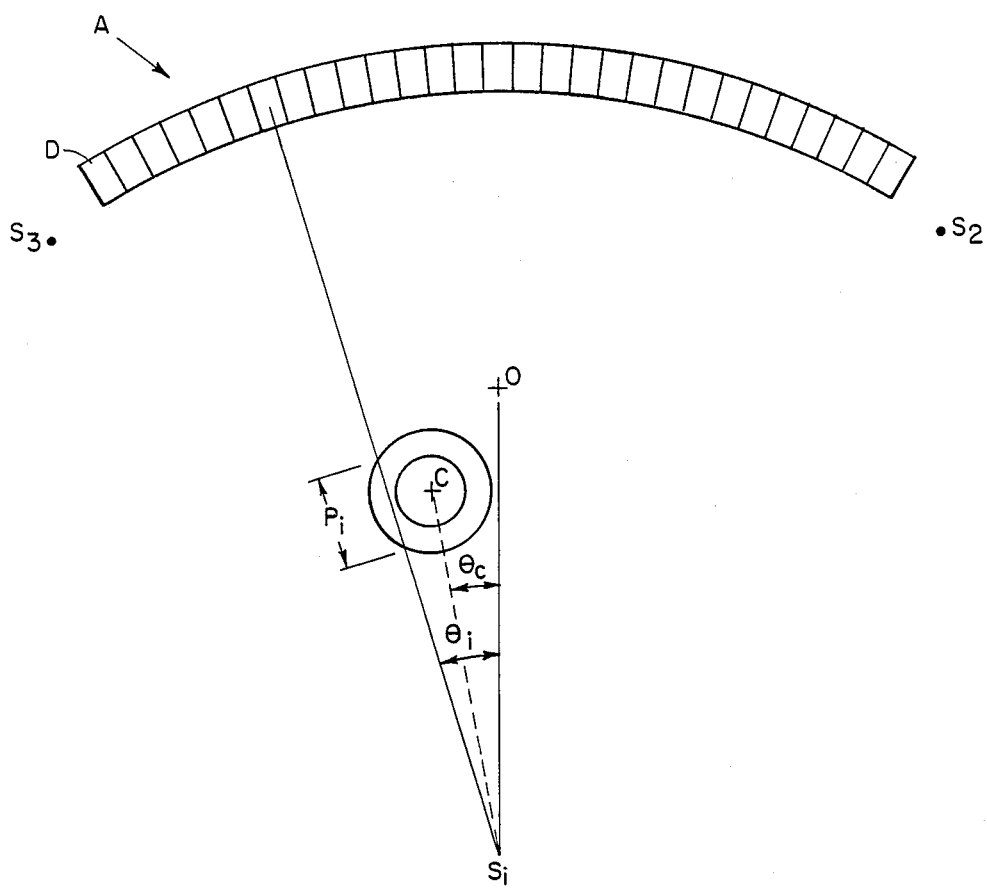
FIG. 8a is a simplified diagrammatic representation showing the relationship among various modeling parameters of the circle calculation algorithm used in the computer-assisted processing system of the present invention.

Considering the novel computer program in more detail, since $\mu$ and $\rho$ are known values for the product, the chord length $p_i$ along a given path that a photon travels through the product (FIG. 8a), can theoretically be computed from the average density information for any path or ray i from the source to a detector D. As shown in FIG. 8a, the location of a particular path i for which a chord $p_i$ can be computed can be associated with a particular angle $\theta_i$, where $\theta_i$ is the angle between a particular path or ray i and the ray from the same source which passes through the geometric origin O of the apparatus A.

Figure 8B:
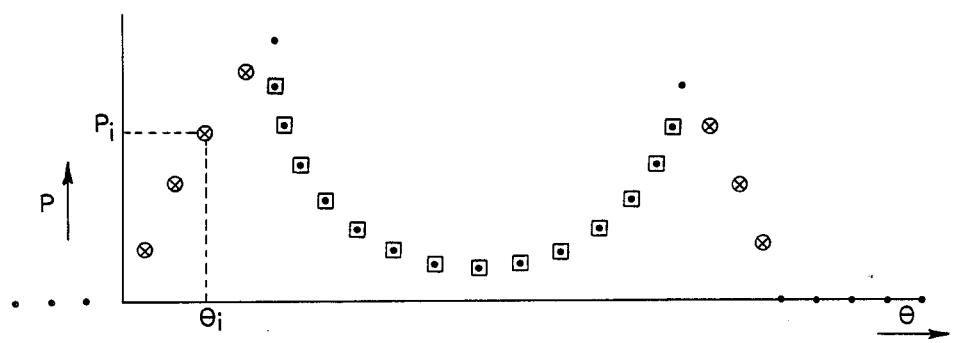
FIG. 8b is a graph of the relationship between modeling parameters of the circle calculation algorithm.
Figure 8C:
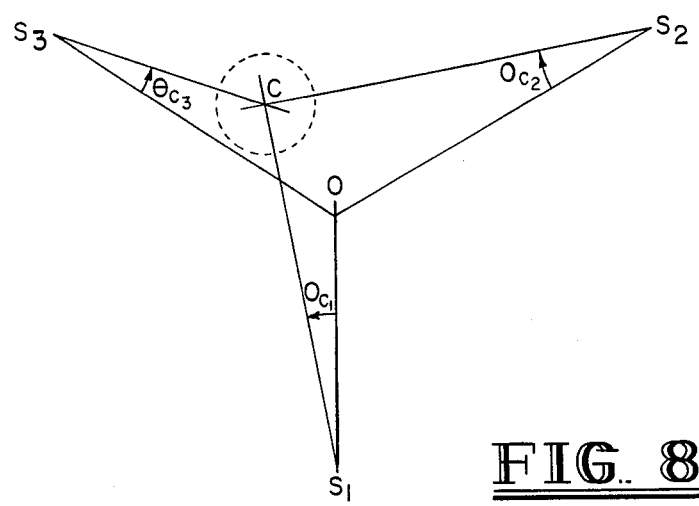
FIG. 8c is a simplified diagrammatic representation of the parameters used by the circle calculation algorithm to determine the centers of the outside and inside circumferences of a tubular product.

FIG. 8b also illustrates that the outside curvature of the original density projection forms a graph which can be used to determine whether a chord $p_i$ at an angle $\theta_i$ is associated with primary radiation which has passed through the product P but which has not passed through the inner cavity of the product P ("outside rays") or primary radiation which has passed both through the product and the inner cavity ("inside rays").

Given the data values of the chords $p_i$ and angles $\theta_i$ for each of the rays i in each of at least two projections, and the known geometry of the sources S and arrays R, the coordinates of the centers Q(x,y) and Q(x',y') and diameters R and R' of the outer circumference and inner circumference forming the product P (FIG. 7) can then be determined by using a novel algorithm to fit a circle to the various chord length data points associated with the outside circumference and the inside circumference (FIG. 8b). This algorithm hereinafter referred to as the "circle calculation method" may be mathematically described as follows:

DIRECT CIRCLE CALCULATION ALGORITHM

For each fan of measurements, ray i is the path from the source $S_i$ to detector $D_i$;

$\theta_i$ is the angle between ray i and the ray from the Source $S_i$ to the geometric center or origin O of the source detector configuration ("source-origin ray"); and $p_i$ is the chord length of the intersection of ray i and the circle to be measured.

To compute $\theta_c$ (the angle between the source-origin ray and the ray from the source to the center of the circle), the computer uses the formula $$\theta_c = \tfrac{1}{2}\tan^{-1}\left(\frac{K_1 \times Q_2 - C_3 \times Q_1}{K_2 \times Q_1 - C_3 \times Q_2}\right)$$

where $K_1 \equiv \Sigma\cos^2(2\theta_i) - \frac{1}{N}(\Sigma\cos(2\theta_i))^2$ $K_2 \equiv \Sigma\sin^2(2\theta_i) - \frac{1}{N}(\Sigma\sin(2\theta_i))^2$ $K_3 \equiv \Sigma(\sin(2\theta_i) \times \cos(2\theta_i)) - \frac{1}{N}(\Sigma\cos(2\theta_i))(\Sigma\sin(2\theta_i))$ $Q_1 \equiv \Sigma\left(\frac{p_i^2}{4} \times \cos(2\theta_i)\right) - \frac{1}{N}\left(\Sigma\frac{p_i^2}{4}\right)(\Sigma\cos(2\theta_i))$ $Q_2 \equiv \Sigma\left(\frac{p_i^2}{4} \times \sin(2\theta_i)\right) - \frac{1}{N}\left(\Sigma\frac{p_i^2}{4}\right)(\Sigma\sin(2\theta_i))$ with the summations over the N rays which intersect the circle under investigation such that the chord lengths $p_i$ are known. These N rays need not be contiguous members of the fan beam; for computation of the outer circle, the rays used will be in two sets (see FIG. 8b).

The three terms $K_1$, $K_2$, and $K_3$ are geometric terms whose values depend only on which rays are in the set of N rays. If a series of partial sums are precomputed for the trigonometric terms, each particular sum can be computed by a single subtraction (for the continuous rays of the inner circle) or by one addition and two subtractions (for the two regions of outside rays). Thus, for example, if $$A(i) = \sum_{j=1}^{i} \cos^2(2\theta_j), \text{ then}$$

$$\sum_{L=30}^{37} \cos^2(2\theta_i) = A(37) - A(29)$$

Figure 8D:
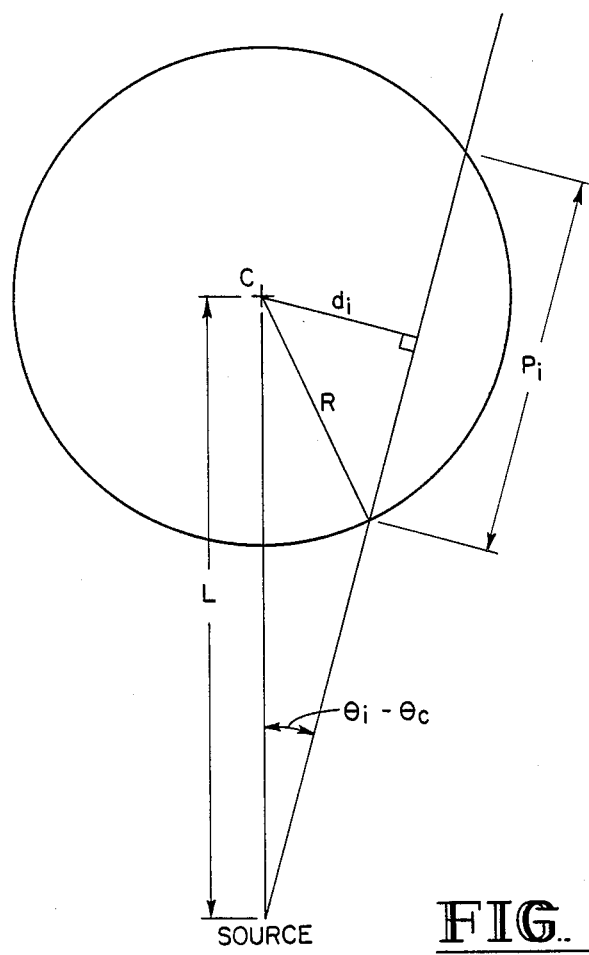
FIG. 8d is a simplified diagrammatic representation of the parameters used by the circle calculation algorithm to determine the radius of the circles formed by the outside and inside circumferences of a tubular product.

Once the value of $\theta_c$ has been computed for each source-detector fan, the position of the circle center C is computed from the intersection of the rays at that angle from each source. From this computed position of C and the known position of each source $S_i$ (FIG. 8d), a source-center distance L can be computed for each fan.

With L and $\theta_c$ known, each measurement $p_i$ provides an estimate of the diameter D as (FIG. 8d):

$$D_i = 2R = 2\sqrt{(p_i/2)^2 + d_i^2} = \sqrt{p_i^2 + 4d_i^2}$$

since $d_i = L \sin(\theta_i - \theta_c)$, $$D_i = \sqrt{p_i^2 + 4L^2\sin^2(\theta_i - \theta_c)}$$

To use all the measurements $p_i$, a root-mean-square average can be computed as $$D = \sqrt{\Sigma D_i^2/N} = \sqrt{(\Sigma(p_i^2 + 4L^2\sin^2(\theta_i - \theta_c))/N}$$

An equivalent form that improves computation speed is $$D = \sqrt{\frac{\Sigma p_i^2}{N} + 2L^2\left(1 - \frac{1}{N}[\cos(2\theta_c) \times \Sigma\cos(2\theta_i) + \sin(2\theta_c) \times \Sigma\sin(2\theta_i)]\right)}$$

As described previously, all summations are over the N rays and precomputed partial sums are used to speed the computation.

It should be noted that the circle calculation algorithm described above can be easily adapted for use with other types of CT scanning apparatus employing fan or parallel beam radiation sources which are capable of being adapted for measuring the dimensions of nominally circular objects.

The processing of density values forming density projections with the use of this circle calculation algorithm provides for numerous advantages over previous methods of measuring the dimensions of tubular products. For example, the noniterative method disclosed in U.S. Pat. No. 4,187,425 computes less accurate on-line dimensional measurements of continuously produced tubular pipe and is sensitive to movements in the position of the pipe. In addition, known iterative techniques, such as the method of least squares, are also too slow for on-line dimensional analysis of continuously produced tubular pipe.

In addition, existing circle fitting techniques used in nonrelated technologies are not suitable for determining the dimensions of tubular products. For example, circle fitting techniques have been used in particle physics research to determine the particle track curvature of a particle from specific coordinates of the interaction points of the particle in the surrounding medium, as disclosed in *Nuclear Instruments and Methods* 211 (1983) 223–225. The circle fitting technique described therein is based on locating the Cartesian coordinates of the center of an arc, given the Cartesian coordinates of the points on that arc.

APERTURE CORRECTION ALGORITHM

While it is mathematically very convenient to treat the ray measurements as resulting from effects along a single straight line, this is an oversimplification. both source and detector apertures extend over a finite extent, so the actual path of the penetrating radiation that reaches a detector may have small displacements in position and angle from the average for that detector. This means that measurements cannot give exact dimensions on a particular geometrical line without further processing which would use additional information. This issue is particularly important when high-speed examination is needed, because in such a case the source and detectors may be large in order to minimize statistical fluctuations.

A method is also used in the invention to convert the measured values of the chords into "ideal" values: the intersection lengths of the central source-detector lines and the product under examination. The method makes use of the fact that the product is known to be nearly circular and that an estimate of diameter is available from the expected or nominal values or an earlier iteration.

The correction function that converts a measured value into an ideal one is a polynomial in three variables: the measured value $p_i$, the diameter estimate $D_i$, and the source-center distance L. The coefficients of the polynomial are precomputed by fitting a function to simulated data.

One or two iterations of this process (alternated with the circle calculation algorithm to improve the estimates of D and L) are enough to remove all significant aperture effects. In addition, the use of this algorithm makes the parameter computations insensitive to the exact registration of the product.

These two algorithms are employed to compute the desired dimensions of each cross section of the tubular product P in accordance with the following steps:

A. Ray Classification

For each projection, find the left and right maxima and the left and right extreme points at which the projected mass is significantly above zero. Then identify as "outside rays" those rays which have some of their components passing through the product but none through the inner cavity. Identify as "inside rays" those rays which pass through the inner cavity. The rays which pass sufficiently close to the maxima on each side so that only part of their components pass through the inner cavity are not counted in either group.

B. Outside Circle Calculation Using Only Outside Rays

1. If an estimate of outside diameter is available from the nominal specifications for the tubular product or an earlier calculation, correct each "outside circle" chord length for source and detector aperture effects using the "aperture correction" algorithm.

2. Using the "circle computation" algorithm, compute the angular position $\theta_c$ of the center of the outside circle from the source-origin ray for each source.

3. Using the angular positions $\theta_c$ for each source projection (FIG. 8d) determine the intersection of the rays at such angular positions in order to locate the center of the outer circle. Compute the Cartesian coordinates of the center of the outer circle Q(x,y).

4. Compute the distances $L_i$ from this computed center of each of the sources.

5. For each source projection, compute an outside diameter (as seen from the particular source) using the "circle calculation" algorithm.

6. If additional accuracy is desired, iterate all the steps in this section B until desired precision is obtained. (One iteration is normally sufficient to obtain the desired accuracy.)

C. Use of Outer Circle Parameters

1. Calculate an average diameter for the outside circle based on the diameters calculated for each projection. If at least three source projections are used, calculate the degree and orientation of the ovality of the outside of the product.

2. For each projection, compute the projected chord lengths $p_i$ that would be measured through a hypothetical solid object having a diameter equal to the computer-generated average diameter for the outside circle.

D. Inner Circle Calculation

1. If estimates of inner diameter and the amount and direction of eccentricity are available from the nominal specifications or from earlier iterations, correct each inside chord length for source and detector aperture effects using the "aperture correction" algorithm.

2. Form a new set of projections by subtracting each corrected actual "inner" length value from the value for the same chord length value computed for a solid tube in C(2). These computed inside chord projections can be taken as equivalent to those expected from a solid object with the same size, shape, and position as the cavity inside the tubular product.

3. Using the "circle computation" algorithm and the computed chord values of D(2), compute the angular position $\theta_c$ of the center of the inside circle from the source-origin ray of each projection.

4. Using the angular positions $\theta_c$ for each source projection, determine the intersection of the rays passing through the center in order to locate the center of the inner circle. Compute the Cartesian coordinates of the center of the inner circle Q(x',y').

5. Compute the distances $L_i$ from center of the computed inner circle to each of the sources $S_i$.

6. For each source projection, compute the diameter of the inner circle using the circle calculation algorithm.

7. If additional accuracy is desired, iterate all the steps in this section D until desired precision is obtained.

E. Use Inner and Outer Circle Parameters and Store Computed Additional Parameters 1. Using the final values calculated for the centers and diameters of the inner and outside circles, compute other parameters of interest such as minimum and average wall thickness, weight per foot, amount and direction of eccentricity, and ovality.

2. Store the values of these additional parameters of each cross section for analysis after the complete product has been examined.

3. Using the final values for the "inner circle" center and diameter, compute "residue" projections for each inside ray as the difference between the value computed in D(2) and the theoretical value of the projection along that ray through a hypothetical solid object with the same shape, size, and position as the cavity inside the tube. Note any high-frequency changes sufficiently in excess of noise to indicate an anomaly in the tube. Accumulate appropriately scaled and shifted projections for several examination periods to reduce the noise ratio in the average.

F. Analysis After Complete Examination of Entire Pipe Length

1. Using the values of the centers and diameters for each scanned cross section of the product, compute the average and extreme values of the parameters of interest over the length of the product or any desired portion thereof.

2. Analyze the accumulated residue projections from E(3) both for the presence of high-frequency anomalies indicating flaws and low-frequency anomalies indicating deviation of the product from the modeled shape.

The information required to determine the diameters and the eccentricity (and thus the average and minimum wall thickness) may be provided by two sets of sources and detector banks. For each fan of measurements provided by such a set, the direct circle calculation algorithm can be applied to give the angular position of the center as seen from the source. The intersection of two lines so determined gives the center locations of outer and inner circles. Combination of the values with the angular width of the projections and the known source positions gives the linear inner and outer diameters as seen from the direction of each source.

When more than two source-detector sets are used, the major effects are:
(a) Quantitative improvement in the measurements already available, due to averaging effects.
(b) Improvement in the visibility of flaws, since
 (i) each flaw is more likely to be in a flatter portion of at least one projection, and
 (ii) compensating flaws are much less likely to cancel in all views.
(c) Some parameters of the product shape can be determined with three or more views that were indeterminate from two views. Illustrative of these, and the most important practically, is the ovality of the tube. While two views may detect ovality if the orientation of the tube is favorable, no reliable estimate of the amount of ovality can be made because any difference in diameters may be partially masked by the orientation of the tube. From three or more views, however, the amount of ovality can be calculated dependably, since only a unique combination of ovality and orientation would cause any particular set of three apparent diameters.

In addition to the estimation of dimensional parameters, the apparatus A can be used to detect pipe flaws such as internal scratches. Although the flaw detection analysis is simpler and faster than the procedure used for dimensional estimation, it is not as precise.

Flaw detection consists mainly of detecting high-frequency changes in the central portion of the residue of each projection. Since each point on the product is usually in the central 60 percent of at least one of the three projections (and the relatively shallow product curvature in that section can be filtered out), this process will detect any flaw of sufficient contrast to its surroundings.

The aperture function that describes the area of the device sensitive to the presence of the tube is about 0.5 inches long, along the direction of tube motion. At the maximum speed of 5 feet per second, data scans are needed every 8 milliseconds plus the exposure time to have all of the pipe examined. In practice, it has been found that any flaws that are relatively long can be detected by less frequent sampling.

IV. OPERATION

With the present invention, a manufacturer can perform measurements on many products, including seamless, extruded, stretched or welded steel tube, moving up to five feet per second and vibrating at two to three cycles per second with an amplitude of $\pm 0.5''$. The invention does not require exact positioning of the product P to give accurate measurements. Hollow steel products P of less than 2.0 inch wall thickness can be inspected. Products can be inspected hot, at 2000 degrees F. for example, or cold. Measurements can be made from 10 to 100 times per second, resulting in virtually continuous measurement and near instantaneous readout. For a single 0.1 second exposure of half-inch wall thickness tube, the standard deviation of the individual measurements in the central area of the projection would be about 0.003 inches for a gamma ray source containing 20 curie of Co-60.

In addition, the data also allows for the detection of flaws. For example, 0.1 inch wide flaws with depths of 0.003 inches can be reliably detected. Narrower flaws of proportionally greater depth can also be seen.

The foregoing disclosure and description of the invention are illustrative and explanatory thereof, and various changes in the size, shape, and materials as well as in the details of the illustrated construction may be made without departing from the spirit of the invention.

What is claimed is:

1. Apparatus for determining measurements on and detecting flaws in tubular or cylindrical objects of known density having an outer circumference and an inner circumference, comprising:
 (a) a plurality of transmitting means angularly disposed about the object to be measured for transmitting a fan beam of known intensity containing a plurality of photons of penetrating radiation along a plurality of paths toward a cross section of the object to be measured;
 (b) a plurality of detecting means angularly disposed about the object for detecting photons wherein each of said detecting means is disposed opposite one of said transmitting means for detecting the plurality of photons passing through a cross section of the object from said transmitting means along each path for generating signals representative of the number of photons detected along each of the plurality of paths;
 (c) mounting means on which said plurality of transmitting means and detecting means are mounted stationary relative to the other; and,
 (d) processing means for processing the signals from said detecting means to generate measurements of thickness, interior and exterior dimensions, eccentricity, and weight-per-unit-length for the object;

wherein said processing means includes computing means which:
(i) determines the length of the portion of each path which passes through any solid portion of the object from the known density of the object and the density signals associated with each path;
(ii) classifies each length signal as an air region signal, outside region signal and inner region signal;
(iii) corrects each outside region signal for aperture effects;
(iv) determines the coordinates of the center and the diameter of the outer circumference of the object from the outer region signals;
(v) calculates length signals for a hypothetical solid object having the same center coordinates and diameter as the outer circumference of the object;
(vi) subtracts inner region signals from the length signals of the hypothetical solid object to form inside circle length signals;
(vii) determines the coordinates of the center and the diameter of the inner circumference of the object from the inside circle length signals; and
(viii) computes other measurements, such as eccentricity and thickness, from the coordinates of the centers and diameters of the inner circumference and outer circumference of the object.

2. The apparatus of the claim 1, wherein:
(a) said computing means also generates residue signals by subtracting the real inner circle length signals from corresponding length signals of a hypothetical solid object having the same center and diameter of the cavity formed by the inner circumference; and
(b) said processing further includes means for analyzing the frequency changes in the residue signals wherein such frequency changes are representative of flaws.

3. The apparatus of claim 1, wherein:
(a) there are at least three transmitting means and at least three detecting means disposed about the object at regular intervals; and
(b) said computing means generates measurements of ovality.

4. The apparatus of claim 3, further comprising:
(a) means for continuously moving the object through the apparatus;
(b) means for controlling the transmitting means, detecting means and processing means as the object is moved through the object in order to generate parameter measurements for a plurality of cross sections of the object; and
(c) wherein said processing means generates the average and extreme values of the measurements taken for each cross section of the object and also generates signals representative of flaws by analyzing the frequency variations between residue signals from the plurality of scanned cross sections of the object.

5. The apparatus of claim 1, wherein:
the transmitting means transmit photons within at least one energy range of photons wherein the energies of the photons within such energy range do not vary more than 15% from the energy of any other photon within such energy range, and the photons within such energy range are at least 50% more energetic than any other significant group of photons emitted at lower energies.

6. The apparatus of claim 5, wherein said transmitting means comprises:
an isotopic Co-60 gamma ray source.

7. The apparatus of claim 5, wherein said transmitting means comprises:
an isotopic Cs-137 gamma ray source.

8. The apparatus of claim 5, wherein said detecting means comprises:
(a) high speed scintillator means for detecting both secondary and primary photons and generating bundles of light photons in response to the detection of primary or secondary photons;
(b) photomultiplier means optically coupled to said scintillator means for detecting the bundle of light photons associated with each penetrating ray photon detected and generating a current signal for each penetrating ray photon detected;
(c) discriminator means for generating primary signals in response to each current signal from the photomultiplier means which exceeds a specified threshold signal magnitude from said processing means wherein the magnitude of the threshold signal is set sufficiently high to prevent the generation of primary signals in response to signals from the photomultiplier means which have magnitudes representative of secondary photons;
(d) means for counting the primary signals generated by said discriminator means.

9. The apparatus of claim 8, wherein said discriminator means comprises:
(a) pulse amplifier means for generating output voltage signals in response to the current signals from the photomultiplier means wherein the voltage signals are proportional to the current signals;
(b) closed loop discriminator for generating primary signals in response to voltage signals from said pulse amplifier means; and
(c) means for individually controlling the threshold signal magnitude for said closed loop discriminator.

10. A method for determining measurements on and deflecting flaws in tubular or cylindrical objects of known density having an outer circumference and an inner circumference, comprising:
(a) transmitting a plurality of fan beams of penetrating radiation of known intensity toward the object to be measured from different angles, wherein each fan beam contains a plurality of photons which pass through the object along a plurality of paths;
(b) detecting the plurality of photons in each fan beam which pass through the object along each of the paths;
(c) generating signals representative of the number of photons detected along each of the plurality of paths;
(d) determining the average density of the plurality of photons along each of the plurality of paths and generating density signals for each path; and
(e) processing the density signals to determine measurements of thickness, interior and exterior dimensions, eccentricity and weight per unit length, wherein the step of processing comprises:
(i) determining the length of the portion of each path which passes through the solid portion of the object from the known density of the object and the density signal associated with each path;

(ii) classifying each length signal as an air region signal, outside region signal and inside region signal;

(iii) correcting each outside region signal for aperture effects;

(iv) determining the coordinates of the center and the diameter of the outer circumference of the object from the outer region length signals;

(v) calculating length signals for a hypothetical solid object having the same center coordinates and diameter as the outer circumference of the object;

(vi) subtracting real inner region signals from corresponding length signals of the hypothetical solid object to form inside circle length signals;

(vii) determining the coordinates of the center and the diameter of the inner circumference of the object from the inside circle length signals; and (viii) computing other measurements, such as eccentricity and thickness, from the coordinates of the centers and diameters of the inner circumference and outer circumference of the object.

11. The method of claim 10, wherein said step of processing further compromises:

(a) generating residue signals by subtracting the real inner circle length signals from corresponding length signals of a hypothetical solid object having the same center and diameter as the cavity formed by the inner circumference; and (b) analyzing the frequency changes in the residue signals wherein such frequency changes are representative of flaws.

12. The method of claim 11, further comprising:
continuously moving the object through the apparatus in order that the steps of transmitting, detecting, and processing are repeated for a plurality of cross sections of the object.

13. The method of claim 10, wherein:
the transmitted photons include photons within at least one energy range of photons wherein the energies of the photons within such energy range do not vary more than 15% from the energy of any other photon within such energy range, and the photons within such energy range are at least 50% more energetic than any other significant group of photons emitted at lower energies.

14. The method of claim 13, wherein the step of detecting comprises:

(a) detecting both secondary and primary photons and generating bundles of light photons in response to the detection of primary or secondary photons;

(b) detecting the bundle of light photons associated with each penetrating ray photon detected, and generating a signal for each penetrating ray photon detected; and (c) generating primary signals in response to each signal which exceeds a specified threshold signal magnitude wherein the magnitude of the threshold signal is set sufficiently high to prevent the generation of primary signals in response to the signals which have magnitudes representative of secondary photons.

15. A method for determining measurements on and deflecting flaws in tubular or cylindrical objects of known density having an outer circumference and an inner circumference, comprising:

(a) transmitting a plurality of fan beams of penetrating radiation of known intensity toward the object to be measured from different angles, wherein each fan beam contains a plurality of photons which pass through the object along a plurality of paths;

(b) detecting the intensity of the transmitted radiation which passes through the object along each of the plurality of paths;

(c) generating signals representative of the intensity of the radiation detected along each of the plurality of paths;

(d) determining the average density of the object along each of the plurality of paths and generating density signals representative of the average density of the object along each path; and (e) processing the density signals to determine measurements of thickness, interior and exterior dimensions, eccentricity and weight per unit, wherein said step of processing comprises:

(i) determining the length of the portion of each path which passes through the solid portion of the object from the known density of the object, and the attenuation signals associated with each path;

(ii) classifying each length signal as an air region signal, outside region signal and inside region signal;

(iii) correcting each outside region signal for aperture effects;

(iv) determining the coordinates of the center and the diameter of the outer curcumference of the object from the outer region length signals;

(v) calculating length signals for a hypothetical solid object having the same center coordinates and diameter as the outer circumference of the object;

(vi) subtracting real inner region signals from corresponding length signals of the hypothetical solid object to form inside circle length signals;

(vii) determining the coordinates of the center and the diameter of the inner circumference of the object from the inside circle length signals; and (viii) computing other measurements, such as eccentricity and thickness, from the coordinates of the centers and diameters of the inner circumference and outer circumference of the object.

16. The method of claim 15, wherein said step of processing further comprises:

(a) generating residue signals by subtracting the real inner circle length signals from corresponding length signals of a hypothetical solid object having the same center and diameter as the cavity formed by the inner circumference; and (b) analyzing the frequency changes in the residue signals wherein the frequency changes are representative of flaws.

17. Apparatus for determining measurements on and detecting flaws in tubular or cylindrical objects of known density having an outer circumference and an inner circumference, comprising:

(a) a plurality of transmitting means angularly disposed about the object to be measured for transmitting a fan beam of known intensity containing a plurality of photons of penetrating radiation along a plurality of paths toward a cross section of the object to be measured wherein each of said transmitting means transmit photons within at least one energy range of photons, the energies of the photons within such energy range do not vary more than 15% from the energy of any other photon within such energy range, and the photons within such energy range are at least 50% more energetic than any other significant group of photons emitted at lower energies;

(b) a plurality of detecting means angularly disposed about the object for detecting photons wherein each of said detecting means is disposed opposite one of said transmitting means for detecting the plurality of photons passing through a cross section of the object from said transmitting means along each path for generating signals representative of the number of photons detected along each of the plurality of paths;

(c) mounting means on which said plurality of transmitting means and detecting means are mounted stationary relative to the other;

(d) processing means for processing the signals from said detecting means wherein said processing means generates signals representative of the average density of the object along each path and then generates measurements of thickness, interior and exterior dimensions, eccentricity, and weight-per-unit-length for the object from the density signals for each path.

* * * * *